United States Patent [19]

Larue

[11] Patent Number: 5,601,234
[45] Date of Patent: Feb. 11, 1997

[54] FLUID NOZZLE AND METHOD OF INTRODUCING A FLUID

[75] Inventor: Roderick W. Larue, Sebastopol, Calif.

[73] Assignee: Abbott Laboratories, Abbott Park, Ill.

[21] Appl. No.: 356,432

[22] Filed: Dec. 15, 1994

Related U.S. Application Data

[63] Continuation-in-part of Ser. No. 283,379, Aug. 1, 1994, abandoned.

[51] Int. Cl.$^6$ .............................. B05B 17/04; B05B 15/02
[52] U.S. Cl. .............................................. 239/1; 239/119
[58] Field of Search .................................. 239/428, 424, 239/422, 119, 113, 112, 106, 104, 1; 436/63; 356/39, 73, 246

[56] References Cited

U.S. PATENT DOCUMENTS

| | | | |
|---|---|---|---|
| 3,795,149 | 3/1974 | Gillette et al. | 73/423 |
| 4,221,339 | 9/1980 | Yoshikawa | 239/424 X |
| 4,348,107 | 9/1982 | Leif | 356/73 X |
| 4,352,558 | 10/1982 | Eisert | 356/39 |
| 4,515,274 | 5/1985 | Hollinger et al. | 356/73 X |
| 4,538,921 | 9/1985 | Kennedy | 239/424 X |
| 4,544,095 | 10/1985 | Litzen | 239/424 X |
| 5,007,732 | 4/1991 | Ohki et al. | 356/39 X |
| 5,030,002 | 7/1991 | North, Jr. | 356/73 |
| 5,138,181 | 8/1992 | Lefevre et al. | 356/73 X |

FOREIGN PATENT DOCUMENTS

| | | |
|---|---|---|
| 0425381 | 5/1991 | European Pat. Off. . |
| 2077457 | 12/1981 | United Kingdom . |

OTHER PUBLICATIONS

Patent Abstracts of Japan vol. 14 No. 512 (P–1129) 9 Nov. 1990.
Patent Abstracts of Japan vol. 14 No. 025 (P991) 18 Jan. 1990.

*Primary Examiner*—Lesley D. Morris
*Attorney, Agent, or Firm*—Mark C. Bach

[57] ABSTRACT

According to one embodiment, a nozzle for introducing a fluid comprises a first conduit having a first end and a second conduit having a second end. The second conduit is disposed substantially concentrically with the first conduit. The first end is offset from the second end. A third conduit having a third end is provided with the third conduit being disposed substantially concentrically with the first conduit and the second conduit and the third end being offset from the first end and the second end. Another embodiment provides a method wherein a first fluid conveying conduit, a second fluid conveying conduit and a third fluid conveying conduit are provided. The second fluid conveying conduit substantially surrounds the first fluid conveying conduit and the third fluid conveying conduit substantially surrounds both the first fluid conveying conduit and the second fluid conveying conduit. A first fluid flows through the first fluid conveying conduit. A second fluid flows through the second fluid conveying conduit. A third fluid flows through the third fluid conveying conduit. Both the second fluid conveying conduit and the first fluid conveying conduit are substantially simultaneously cleaned.

7 Claims, 4 Drawing Sheets

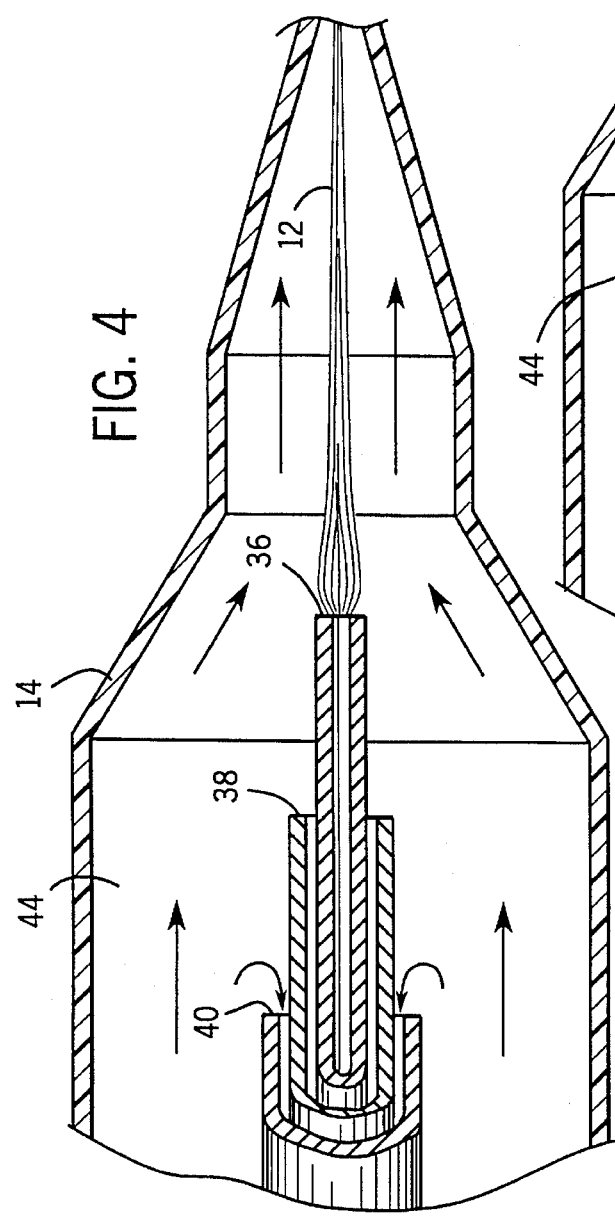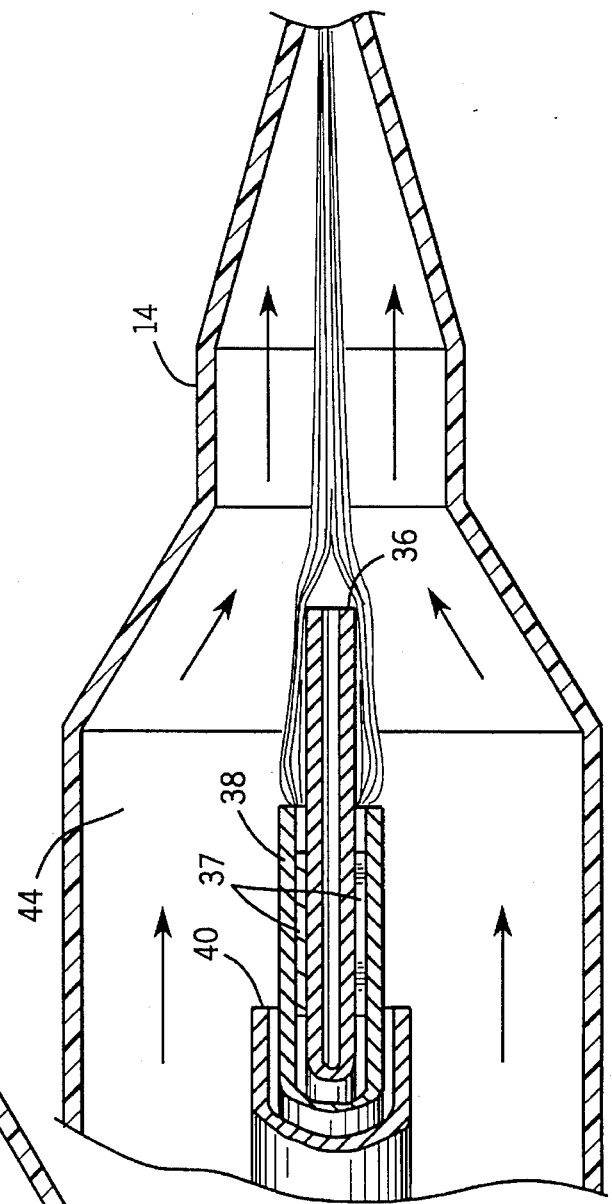

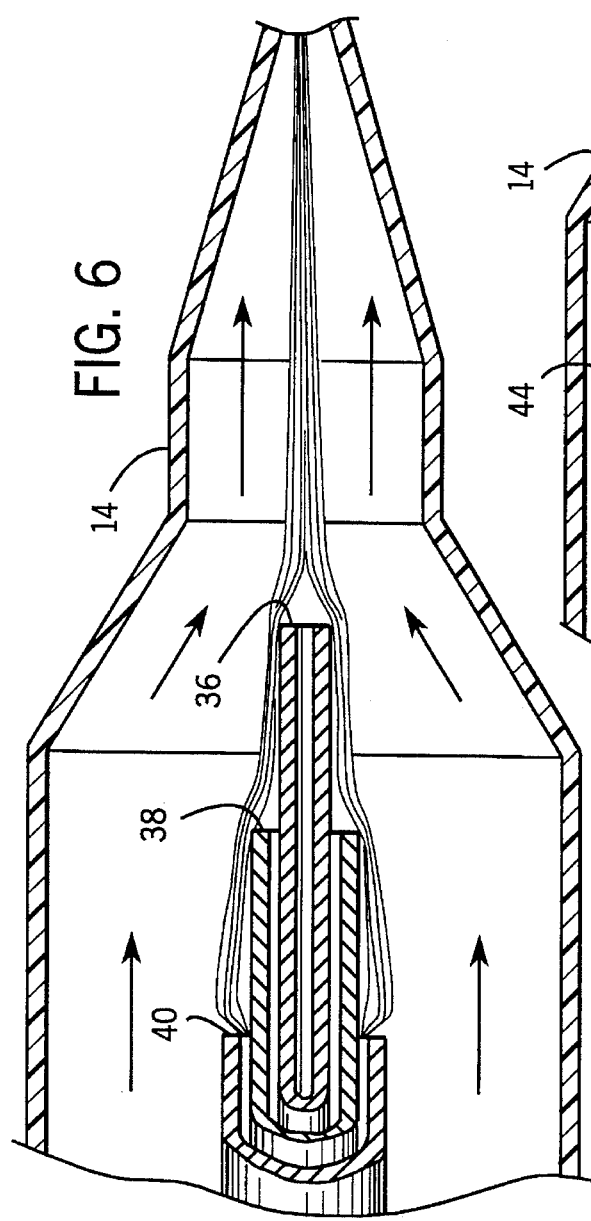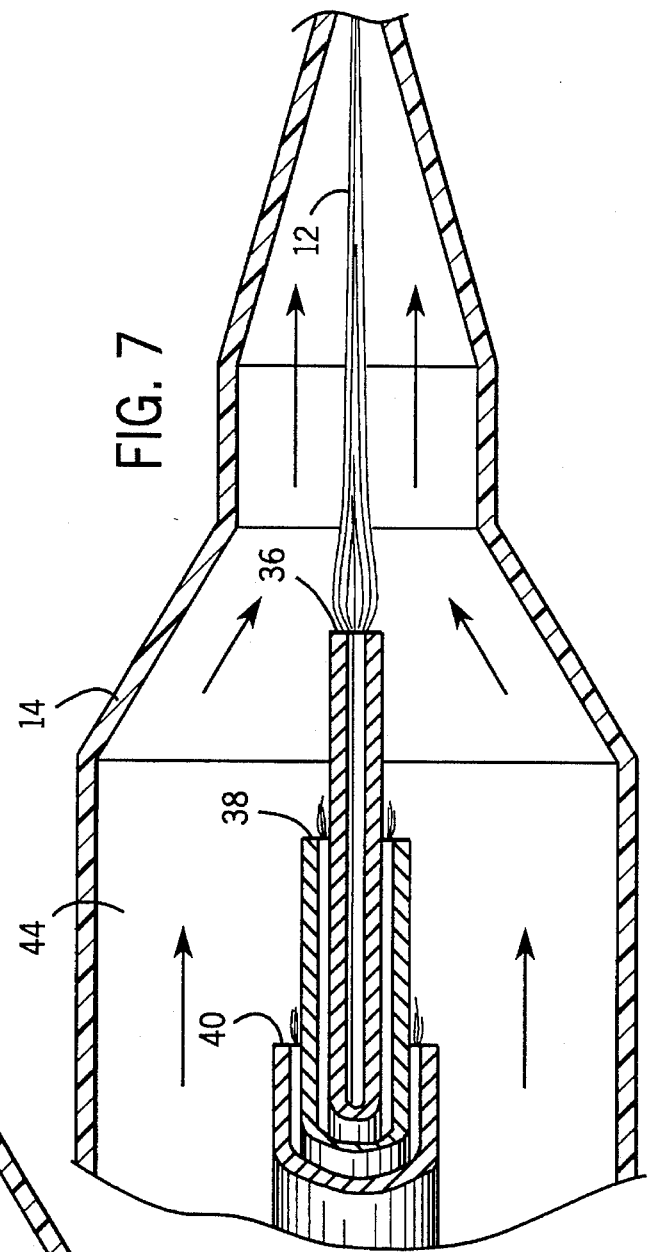

FLUID NOZZLE AND METHOD OF INTRODUCING A FLUID

REFERENCE TO RELATED APPLICATIONS

This is a continuation-in-part application of Ser. No. 08/283,379 filed Aug. 1, 1994, now abandoned entitled METHOD AND APPARATUS FOR PERFORMING AUTOMATED ANALYSIS. The parent application is assigned to the assignee of this case. The disclosure of the parent application is incorporated herein in its entirety by this reference.

BACKGROUND OF THE INVENTION

Embodiments disclosed herein relate generally to a structure, such as a nozzle and the like, and a method for introducing a fluid. More specifically, the embodiments relate to a fluid nozzle and a method of introducing a fluid employable with an automated analytical instrument, such as the instrument disclosed in the above-cited U.S. patent application.

Automated analytical instruments are available to perform a number of tasks. For instance, the automated instrument may perform a number of tests on a fluid, a biological sample and the like. In some embodiments, the fluid on which the tests are performed is a blood sample. The tests performed on the blood sample can be used to determine health status of an individual from whom the blood sample came.

To perform the tests on the blood sample, a portion of the blood sample may be mixed with another fluid, such as a reagent and the like. The blood sample, or the blood sample mixed with the other fluid, is sent to a detector. The detector measures or detects presence of an item of interest in the blood sample. The item of interest may be a cell, a particle and the like. The detector "reads" the blood sample and reports data to a computer. The computer processes the data and reports a result, which indicates presence of the item of interest in the blood sample, to an operator of the instrument.

To introduce or to send the blood sample to the detector, a nozzle of sorts may be used. The blood sample flows through the nozzle toward the detector. As the instrument performs tests on a number of blood samples, it is desirable to clean the nozzle periodically. This cleaning reduces the likelihood that a part of the blood sample from one patient might be mixed with a part of the blood sample from another patient. If blood samples from two patients were to mix, then the analytical instrument may give the operator improper results.

In a desire to avoid improper results, the nozzle may be cleaned after each blood sample flows through the nozzle. Thus, a first blood sample flows through the nozzle, the nozzle is cleaned, and then a second blood sample flows through the nozzle. In addition, some fluids, such as auromine O, acridin orange and the like, that flow through the nozzle may stain or contaminate the nozzle. The staining of the nozzle may reduce the sensitivity or accuracy of the detector possibly causing some sample to be read improperly. It may not be easy to remove this stain. Because the nozzle is cleaned each time a blood sample flows through the nozzle, the time needed to test a given blood sample may be relatively long, especially when multiple samples share a common detector. Given the high demand for medical services and medical tests, it is desired to find a way to reduce the time needed to test a blood sample or other fluid of interest.

SUMMARY OF THE INVENTION

According to one embodiment, a nozzle for introducing a fluid comprises a first conduit having a first end and a second conduit having a second end. The second conduit is disposed substantially concentrically with the first conduit. The first end is offset from the second end. A third conduit having a third end is provided with the third conduit being disposed substantially concentrically with the first conduit and the second conduit and the third end being offset from the first end and the second end.

Another embodiment provides a method wherein a first fluid conveying conduit, a second fluid conveying conduit and a third fluid conveying conduit are provided. The second fluid conveying conduit substantially surrounds the first fluid conveying conduit and the third fluid conveying conduit substantially surrounds both the first fluid conveying conduit and the second fluid conveying conduit. A first fluid flows through the first fluid conveying conduit. A second fluid flows through the second fluid conveying conduit. A third fluid flows through the third fluid conveying conduit. Both the second fluid conveying conduit and the first fluid conveying conduit are substantially simultaneously cleaned.

In an additional embodiment, a first fluid conveying conduit and a second fluid conveying conduit are provided with the second fluid conveying conduit substantially surrounding the first fluid conveying conduit. A first fluid flows through the first fluid conveying conduit at a first fluid flow rate. A second fluid flows through the second fluid conveying conduit at a second fluid flow rate. The first fluid flow rate and the second fluid flow rate are predetermined such that a fluid flow rate differential exists.

In a further embodiment, a first fluid conveying conduit and a second fluid conveying conduit are provided. The second fluid conveying conduit substantially surrounds the first fluid conveying conduit. A detector is operatively associated with the first fluid conveying conduit and the second fluid conveying conduit. A first fluid flows through the first fluid conveying conduit toward the detector. A second fluid flows through the second fluid conveying conduit toward the detector. The first fluid and the second fluid are fluidly focused on the detector.

In another embodiment, a first fluid conveying conduit is fluidly connected with a source of first fluid. A second fluid conveying conduit is fluidly connected with a source of second fluid. The second fluid conveying conduit substantially surrounds the first fluid conveying conduit such that second fluid in the second fluid conveying conduit does not encounter the first fluid in the first fluid conveying conduit. The first fluid flows through the first fluid conveying conduit. The second fluid flows through the second fluid conveying conduit such that the second fluid does not encounter the first fluid.

BRIEF DESCRIPTION OF THE DRAWINGS

FIG. 4 is a sectional view of a portion of the nozzle of FIG. 2 illustrating fluid introduction;

FIG. 5 is a sectional view substantially similar to that of FIG. 4 illustrating fluid introduction;

FIG. 6 is a sectional view substantially similar to that of FIG. 5 illustrating fluid introduction; and FIG. 7 is a sectional view substantially similar to that of FIG. 4 illustrating fluid introduction.

DETAILED DESCRIPTION OF PREFERRED EMBODIMENTS

Figure 2:
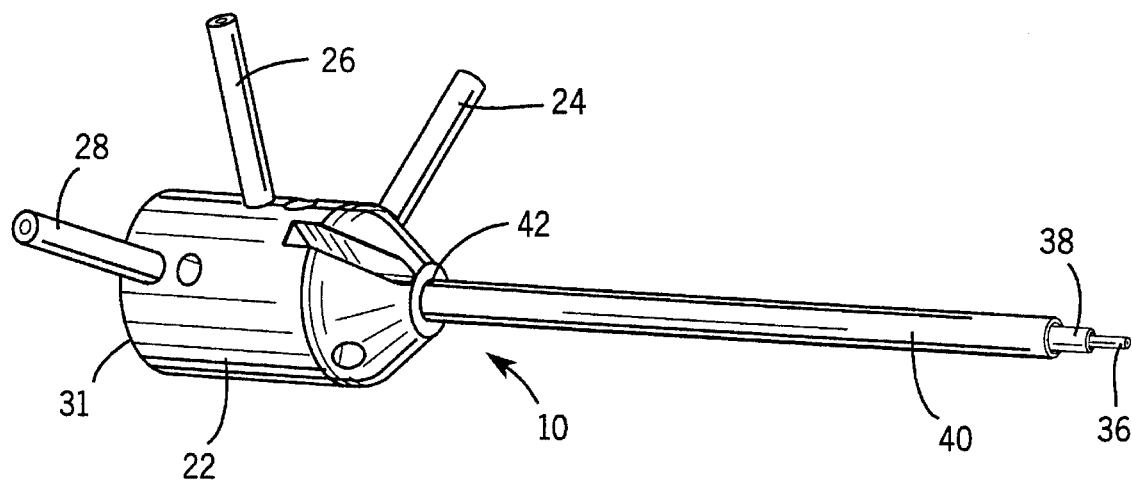
FIG. 2 is a perspective view of the nozzle of FIG. 1.

As shown in FIG. 2, embodiments disclosed herein relate to a fluid nozzle 10 and a method for introducing a fluid 12. For the sake of clarity and understanding, the fluid nozzle 10 is discussed with respect to its employment with an automated analytical instrument, such as the instrument disclosed in the above-referenced U.S. patent application. But, other employments are also possible. Also, to provide the reader with greater understanding, the fluid 12 involved is the fluid used in the analytical instrument. However, other fluids can be used. Furthermore, elements of one embodiment may be combined with elements of another embodiment to arrive at yet other embodiments. For instance, steps from one method may be combined with steps of another method to arrive at yet another method.

Figure 1:
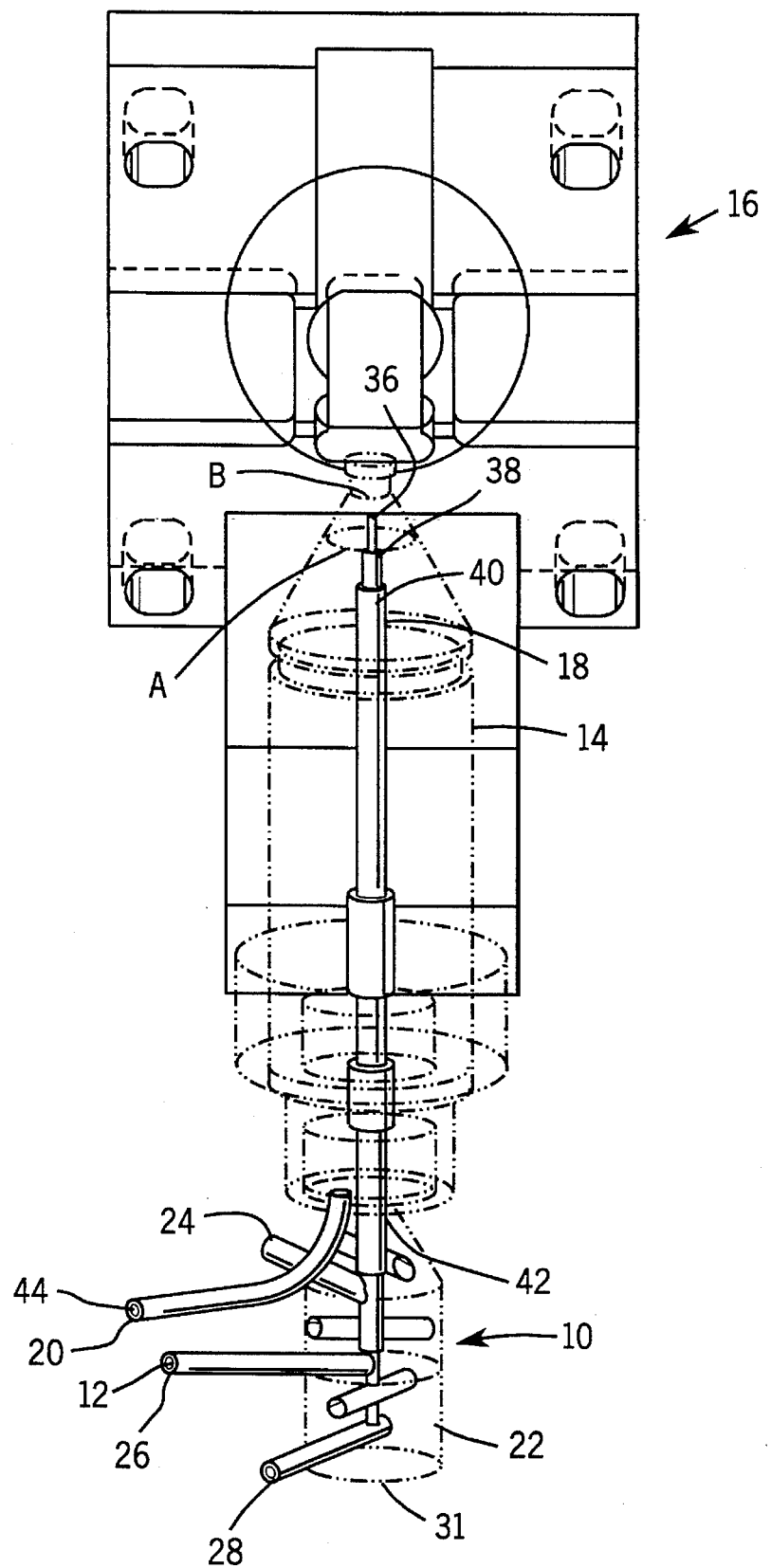
FIG. 1 is a generic elevational view of an apparatus containing a nozzle for introducing a fluid.

In one employment, illustrated in FIG. 1, the fluid nozzle 10 is operatively associated with a conduit or a fluid 12 flow guide 14 and a detector 16 that detects an item of interest, such as a cell, a particle and the like, present in the fluid 12. In the illustrated embodiment, the flow guide 14 comprises a conduit formed from a suitable material, such as a polymer like acrylic, including a bore 18 for accepting the fluid nozzle 10. The fluid nozzle 10 is substantially centered with respect to the flow guide 14 to facilitate direction of fluid 12 from the fluid nozzle 10 to the detector 16. A conduit 20 is fluidly connected with the bore 18 such that a desired fluid 44 from a suitable source may be deposited in the bore 18 through the conduit 20. The detector 16, in an exemplary embodiment, may be an optical flow cell that measures the item of interest in the fluid 12 as the fluid 12 flows from the fluid nozzle 10 through the detector 16. The detector 16 may be used, in some embodiments, to perform a white blood cell differential analysis, platelet analysis and/or reticulocyte analysis, as described in the above-cited U.S. patent application. In those embodiments, preparatory steps for each analysis may be performed in processing paths, which may be separate, and the analysis may be performed in a single detector 16.

Figure 3:
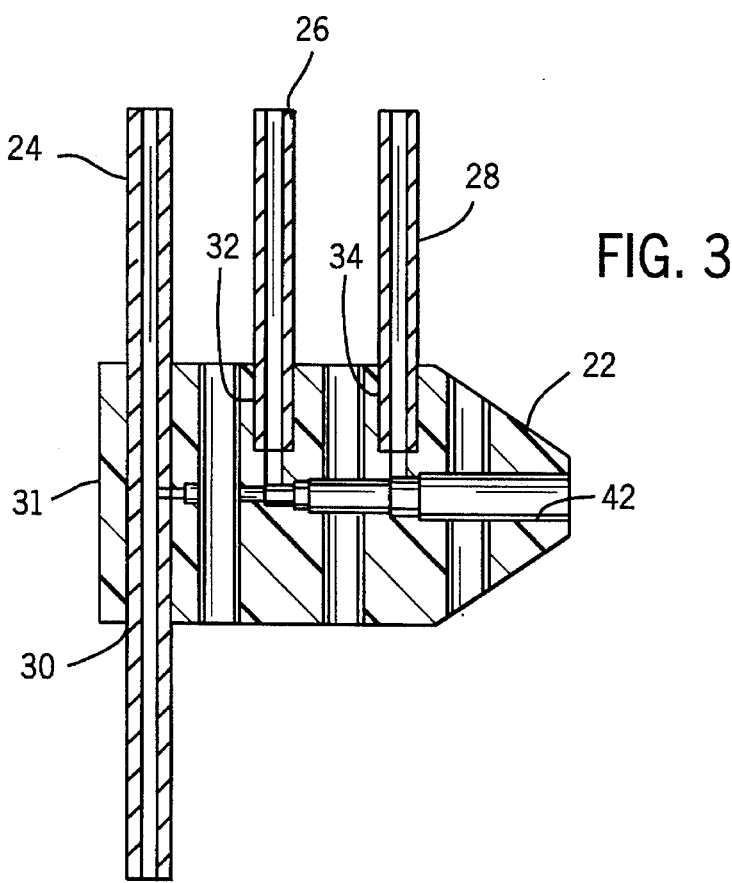
FIG. 3 is a sectional view of a portion of the nozzle of FIG. 2 with conduits shown in FIG. 2 being arranged mutually parallelly for clarity.

The construction of the fluid nozzle 10 is illustrated more clearly in FIGS. 2 and 3. The fluid nozzle 10 generally comprises a manifold 22 and a plurality of conduits fluidly connected with the manifold 22. The exact number of conduits may be chosen to facilitate a particular employment of the fluid nozzle 10. Specifically, in an exemplary embodiment, a first conduit 24, a second conduit 26 and a third conduit 28 are fluidly connected with one portion of the manifold 22. The conduits 24, 26 and 28 may be used as fluid 12 inputs. Thus, the conduits 24, 26 and 28 may be fluidly connected with suitable sources of desired fluid 12.

In a particular embodiment, the manifold 22 is made from a suitable polymer, such as acrylic and the like, and has an axial length of about 0.7 inches. The conduits 24, 26 and 28 are made from a suitable metal, such as 316 stainless steel and the like. The conduit 24 may have an axial length of about 1.14 inches, an inner diameter of about 0.023 inches and an outer diameter of about 0.0625 inches. The conduits 26 and 28 may have an axial length of about 0.5 inches, an inner diameter of about 0.019 inches and an outer diameter of about 0.0625 inches. The outer diameter surfaces of the conduits 24, 26 and 28 may be coated with an adhesive, such as an epoxy and the like, and inserted into complementary bores 30, 32 and 34, respectively, formed in the manifold 22. In the illustrated embodiment, the conduits 24, 26 and 28 are offset axially and circumferentially on the manifold 22. The conduit 28 is offset axially about 0.07 inches from an end 31 of the manifold 22. The conduit 26 is offset about 0.26 inches from the end 31 and the conduit 28 is offset about 0.45 inches axially from the end 31. Circumferentially, the conduit 24 is offset about 60 degrees from the conduit 26 and the conduit 28 is offset about 60 degrees from the conduit 26. Thus, the conduit 24 is offset about 120 degrees from the conduit 28.

The manifold 22 fluidly connects the conduits 24, 26 and 28 with conduits 36, 38 and 40, respectively, which are also operatively associated with the manifold 22. The manifold 22 can allow one of the conduits 36, 38 and 40 to be dedicated to a particular fluid or test run by the instrument with which the nozzle 10 is associated.

The conduits 36, 38 and 40 are disposed substantially coaxially and substantially centrally with respect to the flow guide 14. The disposition of the conduits 36, 38 and 40 with respect to the fluid guide 14 and the detector 16 may be chosen to provide intended positional accuracy of the flow of fluid 12 from the nozzle 10 to the detector 16. The manifold 22 includes a bore 42 for accepting the substantially coaxial disposition of the conduits 36, 38 and 40. The manifold 22 allows fluid 12 in conduits 24, 26 and 28 to flow through the manifold 22 and into conduits 36, 38 and 40, respectively. The conduits 36, 38 and 40 are substantially linear over their entire length. However, in some embodiments, to preserve the coaxial disposition of the conduits 36, 38 and 40, a spacer 37 (FIG. 51) may be provided radially between conduits 36 and 38 and between conduits 38 and 40. The spacer is configured, such as by providing outer diameter surface reliefs, channels and the like, so as not to interfere with fluid 12 movement in the conduits 36, 38 and 40. While the illustrated embodiment shows distal ends of the conduits 36, 38 and 40 being mutually axially offset, this is not necessary.

In an exemplary embodiment, the conduit 36 is made from a suitable metal, such as 304 stainless steel, #3 (full hard) temper hypodermic needle tubing and the like. The conduit 36 has an axial length of about 2.55 inches, an inner diameter of about 0.013 inches and an outer diameter of about 0.025 inches. The conduit 38 is also made from a suitable metal, such as 304 stainless steel, #3 (full hard) temper hypodermic needle tubing and the like. The conduit 38 has an inner diameter of about 0.038 inches, an outer diameter of about 0.050 inches and an axial length of about 2.26 inches. The conduit 40 is made from a suitable metal, such as 304 stainless steel hypodermic needle tubing and the like. The conduit 40 has an inner diameter of about 0.062 inches, an outer diameter of about 0.078 inches and an axial length of about 1.97 inches.

In one embodiment, the flow guide 14 includes a substantially tapered portion having an inner diameter of about 0.25 inches, at point "A", and an inner diameter of about 0.118 inches, at point "B". Both points A and B are labeled in FIG. 1. A relation between relevant conduit 36, 38 and 40 dimensions and corresponding dimensions of the flow guide 14 may be predetermined to provide desired fluid focusing of fluid 12, to reduce a probability of contact between the flow guide 14 and the fluid 12, to optimize detector 16, e.g. optics, operation, etc. In some embodiments, the dimensional relation may be related to the flow rate differential. Specifically, in an exemplary embodiment, a latitudinal cross section of relevant portions of the flow guide 14 is proportional to a related flow rate differential.

In an exemplary embodiment, the tapered portion defines a slope of about 60 degrees. A fluid-conveying portion of the detector 16 adjacent a distal end of the fluid nozzle 10 defines a slope of about 30 degrees with an inner diameter of about 0.118 inches. The dimensions may be chosen to produce intended positional accuracy of the flow of fluid 12 with respect to the detector 16.

If a spacer were provided radially between conduits 38 and 40, then the spacer is made of a suitable metal, such as 304 stainless steel hypodermic needle tubing and the like, having an inner diameter of about 0.051 inches and an outer diameter of about 0.061 inches. If a spacer were provided radially between conduits 36 and 38, then the spacer is made of a suitable metal, such as 304 stainless steel, #3 (full hard) temper hypodermic needle tubing with an inner diameter of about 0.026 inches and an outer diameter of about 0.036 inches. The spacer between the conduits 36 and 38 is located about 0.25 inches proximally of a distal end of the conduit 36. The spacer between the conduits 38 and 40 is positioned immediately proximally of the spacer between the conduits 36 and 38. The spacers have an axial length of about 0.1 inches.

With the construction of the fluid nozzle 10 being thusly disclosed in detail, a method of introducing fluid with the fluid nozzle 10 will now be discussed in detail.

A source of fluid 12, such as blood, a blood component and the like, to be processed by the detector 16 is fluidly connected with one of the conduits 24, 26 or 28 such that fluid 12 flows from the source to the selected conduit 24, 26 or 28. The other conduits 24, 26 or 28 which are not fluidly connected with source of fluid 12 are not supplied with fluid 12. The fluid 12 contains an item of interest, such as a particle, a cell and the like, detectable by the detector 16. In some embodiments, the axial distance among the distal ends of the conduits 36, 38 and 40, along with corresponding fluid flow rates, e.g. positional velocity at fluid introduction point, can be chosen such that fluid 12 Can be introduced through all of the conduits 36, 38 and 40 simultaneously without a significant probability that fluid 12 from different conduits 36, 38 and 40 might interact.

A source of another fluid 44, such as water, a buffer, a fluid that does not adverse react with the fluid 12, and the like, is fluidly connected with the conduit 20 such that the another fluid 44 flows from the source to the conduit 20 and the flow guide 14. The fluid 44 flowing from the conduit 20 into the flow guide 14 surrounds a portion of the conduits 36, 38 and 40 as shown in FIGS. 4 through 6. The offset dispositions of the conduits 36, 38 and 40 permits reduction of fluid 44 flow discontinuities. A gradual reduction in latitudinal cross section of the fluid flow path through the flow guide 14 permits a reduction of the likelihood of fluid diffusion within the flow guide 14. If desired, as fluid 12 flows from one of the conduits 36, 38 or 40, the other two conduits 36, 38 or 40 may be cleaned or "back-flushed" with fluid 44 by applying an appropriate relatively reduced pressure source, for example, to the conduits 36, 38 or 40 being cleaned. Alternatively, after fluid 12 has been sequentially introduced through each of the conduits 36, 38 and 40, all of the conduits 36, 38 and 40 can be simultaneously cleaned by passing an appropriate fluid through the conduits. Thus, because all of the conduits 36, 38 and 40 can be cleaned substantially simultaneously, throughput of the detector 16 can be increased by reducing down time needed to clean the nozzle 10 while also providing for rapid introduction of fluid 12. This also correspondingly can increase the throughput of the analytical instrument with which the detector 16 is associated.

In an exemplary embodiment the flow rate of fluid 44 is larger than the flow rate of fluid 12. For instance, in one embodiment, the flow rate of fluid 12 is about 2.5 µl per second and the flow rate of the fluid 44 is about 300 µl per second. This flow rate differential fluidly directs or focuses the flow of fluid 12 toward the detector 16. This may be desired, for example, if the detector 16 were a flow cell including a laser. In such a case, the flow rate differential can be predetermined such that dimensions of fluid 12 flow into the detector 16 correspond to a beam width, or other dimensions, associated with the laser. Thus, in general, the flow rate differential can be predetermined such that detection of the item of interest in the fluid 12 by the detector 16 is facilitated.

The fluid focusing provided by the flow rate differential is substantially similar irrespective of the conduit 36, 38 or 40 chosen to introduce the fluid 12 as fluid 12 introduced from either conduit 36, 38 or 40 is fluidly focused toward substantially the same position with respect to the detector 16. This allows fluids 12 from each of the conduits 36, 38 and 40, and tests performed by the instrument with which the fluid nozzle 10 is associated, to share the same detector 16. Accordingly, each of the conduits 36, 38 and 40 may be fluidly connected with a separate source of fluid 12 such that the likelihood that fluid 12 from one source might encounter fluid 12 from another source is reduced. Thus, the probability of fluid 12 cross over and/or fluid 12 contamination can be reduced. The fluids 12 from each of the conduits 36, 38 and 40 can be processed by the detector 16 in substantially parallel fashion, thereby improving throughput of the fluid nozzle 10 and the instrument with which the nozzle 10 is associated.

This ability of the fluid nozzle 10 has been verified empirically. In One experiment, illustrated in FIGS. 4 through 6, an exemplary embodiment of the fluid nozzle 10 was analyzed by a finite element method to reveal the fluid properties associated with the nozzle 10. In this embodiment, the conduit 6 has an inner diameter of about 0.013 inches. The distal end of the conduit 38 is offset proximally about 0.29 inches from the distal end of the conduit 36. The conduits 36 and 38 define a substantially annular fluid flow path having an inner diameter of about 0.025 inches and an outer diameter of about 0.037 inches. The distal end of the conduit 40 is offset proximally about 0.29 inches from a distal end of the conduit 38. The conduits 38 and 40 define a substantially annular fluid flow path having an inner diameter of about 0.049 inches and an outer diameter of about 0.061 inches.

The finite element analysis was performed using a FIDAP computer program, version 6.01, available from Fluid Dynamics International of Evanston, Illinois. Steady-state axisymmetric models of fluid flow through the conduits 36, 38 and 40 and steady-state three dimensional models of fluid flow through the detector 16 were analyzed to show that the position of the fluidly focused fluid 12 with respect to the detector 16 is independent of the conduit 36, 38 or 40 used to introduce fluid 12. In all cases, the fluid flow rate of the fluid 44 is about 300 µl per second and the fluid flow rate of the fluid 12 through the chosen conduit 36, 38 or 40 is substantially within the range of about 2.5 µl per second to about 2.0 µl per second. The analyses assumed Newtonian fluid properties with no slip boundary conditions on the solid surfaces.

In one example, to simulate white blood cell differential analysis, platelet analysis, and reticulocyte analysis, three separate fluid analyses were performed. The white blood differential analysis fluid 12 is introduced through the conduit 36, as shown in FIG. 4, at a fluid flow rate of about 2.5 μl per second. As shown in FIG. 5, the platelet analysis fluid 12 is introduced through the conduit 38 also at a fluid flow rate of about 2.5 μl per second. The reticulocyte analysis fluid 12 is directed through the conduit 40, as shown in FIG. 6, at a rate of about 2.0 μl per second. Upon comparison of FIGS. 4 through 6, the fluid flow pathlines from the respective conduits 36, 38 and 40 resulting from the fluid analyses demonstrate that no contamination of a flow of fluid 12 by a prior flow of fluid 12 occurs and that the position of the fluidly focused fluid 12 with respect to the detector 16 is independent of which conduit 36, 38 or 40 is selected.

The independence of the position of the fluidly focused fluid 12 with respect to the detector 16 with respect to the selection of the conduit 36, 38 or 40 is also verified experimentally by optically measuring flow of fluid 12 containing 7 μm diameter beads sequentially through each of the conduits 36, 38 and 40. The fluid 12 containing the beads is introduced at a fluid flow rate of about 2 μl per second.

|            | % C.V., INDEX MATCHED |     |     |
|------------|------|-----|-----|
|            | ALL  | IAS | DSS |
| Conduit 36 | 4.7  | 3.2 | 2.6 |
|            | 4.3  | 3.1 | 2.2 |
| Conduit 38 | 5.0  | 3.6 | 2.0 |
|            | 4.6  | 4.2 | 2.6 |
| Conduit 40 | 4.3  | 3.1 | 2.4 |
|            | 5.1  | 2.8 | 2.7 |

As is evident from the above coefficients of variation, the coefficient of variation (CV) for three measured optical properties (ALL: axial light loss; IAS: intermediate angle scatter; and DSS: depolarized side scatter) are substantially similar for all of the conduits 36, 38 and 40. This similarity in optical response verifies that the fluid nozzle 10 can be used for multiple fluid 12 item of interest measurements prior to any cleaning step, thereby increasing the throughput or analytical capacity of the detector 16 and any instrument associated with the detector 16. The number of fluid 12 measurements or fluid 12 introductions that may occur prior to cleaning corresponds to the number of conduits provided with the fluid nozzle 10. Irrespective of the number of conduits involved, the embodiments described herein allow for substantially simultaneous cleaning of substantially all of the conduits.

If the fluid 12 were to have sufficient propensity to interact with or stick to a portion of the conduits 36, 38 and 40, then remnants of a first fluid in the conduit 36, 38 or 40 may encounter (i.e. carry over) a second fluid passed through the same conduit 36, 38 or 40. Similar concerns are present with the conduits 24, 26 and 28. These concerns may compromise accuracy of the detector 16.

To address these concerns, it is possible to dedicate a specific conduit 36, 38 or 40 to a specific fluid 12 or test performed by the detector 16. The number of conduits 36, 38 and 40 so dedicated may be dependent upon the properties of the fluids 12 being introduced by the fluid nozzle 10. By substantially isolating at least one of the conduits 36, 38 and 40, carry over of one fluid 12 to another fluid 12 can be reduced. For instance, one conduit 36, 38 or 40 could be dedicated to a test that uses a fluid 12 containing a relatively bright fluorescent marker, such as auromine 0 and the like, and another conduit 36, 38 or 40 could be dedicated to a test that uses a fluid containing a relatively dim fluorescent marker. Once the fluids exit the conduits 36, 38 or 40, the volume and flow of fluid 44 through the fluid guide 14 is sufficient to reduce the probability of fluid 12 diffusion while fluidly focusing the fluid 12 toward a common detector 16. Thus, the two tests can be performed substantially sequentially by the same detector 16 without substantially compromising accuracy or sensitivity of the detector 16.

What is claimed is:

1. A method of introducing a fluid, the method comprising the steps of:

(a) providing a first fluid conveying conduit, a second fluid conveying conduit and a third fluid conveying conduit, the second fluid conveying conduit substantially surrounding the first fluid conveying conduit and the third fluid conveying conduit substantially surrounding both the first fluid conveying conduit and the second fluid conveying conduit;

(b) flowing a first fluid through the first fluid conveying conduit;

(c) flowing a second fluid through the second fluid conveying conduit;

(d) flowing a third fluid through the third fluid conveying conduit; and (e) substantially simultaneously cleaning both the second fluid conveying conduit and the first fluid conveying conduit.

2. A method as defined in claim 1 further comprising the step of:

(f) back flushing at least one of the first fluid conveying conduit and the second fluid conveying conduit.

3. A method as defined in claim 1 further comprising the steps of:

(f) flowing at least one of the first fluid through the first fluid conveying conduit and the second fluid through the second fluid conveying conduit at a first fluid flow rate;

(g) flowing the third fluid through the third fluid conveying conduit at a second fluid flow rate; and (h) predetermining the first fluid flow rate and the second fluid flow rate such that a fluid flow rate differential exists.

4. A method as defined in claim 3 further comprising the step of:

(i) fluidly focusing flow of at least one of the first fluid from the first fluid conveying conduit and the second fluid from the second fluid conveying conduit with flow of the third fluid from the third fluid conveying conduit.

5. A method as defined in claim 1 further comprising the step of:

(f) simultaneously flowing first fluid through the first fluid conveying conduit and second fluid through the second fluid conveying conduit.

6. A method of introducing a fluid, the method comprising the steps of:

(a) providing a first fluid conveying conduit and a second fluid conveying conduit substantially surrounding the first fluid conveying conduit and a detector operatively associated with the first fluid conveying conduit and the second fluid conveying conduit;

(b) flowing a first fluid through the first fluid conveying conduit toward the detector;

(c) flowing a second fluid through the second fluid conveying conduit toward the detector;

(d) fluidly focusing the first fluid and the second fluid on the detector; and (e) temporally separating flow of the first fluid and flow of the second fluid.

7. A method of introducing a fluid, the method comprising the steps of:

(a) providing a first fluid conveying conduit fluidly connected with a source of first fluid;

(b) providing a second fluid conveying conduit fluidly connected with a source of second fluid, the second fluid conveying conduit substantially surrounding the first fluid conveying conduit such that second fluid in the second fluid conveying conduit does not encounter the first fluid in the first fluid conveying conduit;

(c) flowing the first fluid through the first fluid conveying conduit;

(d) flowing the second fluid through the second fluid conveying conduit such that the second fluid does not encounter the first fluid.

* * * * *